United States Patent [19]

Sikkenga et al.

[11] Patent Number: 4,777,311

[45] Date of Patent: Oct. 11, 1988

[54] PROCESS FOR CONVERTING $C_5$ OLEFINS TO AROMATIC HYDROCARBONS AND LIGHTER OLEFINS

[75] Inventors: David L. Sikkenga, Wheaton; Christos G. Papadopoulos, Naperville; Paul M. Watson, Downers Grove, all of Ill.

[73] Assignee: Amoco Corporation, Chicago, Ill.

[21] Appl. No.: 72,898

[22] Filed: Jul. 14, 1987

[51] Int. Cl.$^4$ .............................................. C07C 12/02
[52] U.S. Cl. .................................................. 585/415
[58] Field of Search ........................................ 585/415

[56] References Cited

U.S. PATENT DOCUMENTS 4,499,325 2/1985 Klotz et al. ......................... 585/415

Primary Examiner—Curtis R. Davis
Attorney, Agent, or Firm—Gunar J. Blumberg; William H. Magidson; Ralph C. Medhurst

[57] ABSTRACT

A process is disclosed whereby a $C_5$ hydrocarbon stream containing both olefins and paraffins is converted over an AMS-1B crystalline borosilicate catalyst or an AMS-1B crystalline borosilicate composition containing an ion or molecule of a catalytically active element such as a noble metal. The $C_5$ olefins are converted to aromatic hydrocarbons, $C_3$–$C_4$ paraffins and olefins and $C_6$–$C_{11}$ paraffins and olefins.

11 Claims, No Drawings

PROCESS FOR CONVERTING C₅ OLEFINS TO AROMATIC HYDROCARBONS AND LIGHTER OLEFINS

FIELD OF THE INVENTION

The field of this invention relates to a process for converting a $C_5$ stream containing $C_5$ paraffins and $C_5$ olefins to $C_6$-$C_{11}$ paraffins and olefins, aromatic hydrocarbons and lighter olefins. The $C_5$ paraffins remaining in the $C_5$ stream, after the conversion products are separated, are a desirable feedstock for steam cracking.

BACKGROUND OF THE INVENTION

Among the products generated in the steam cracking of hydrocarbons is a $C_5$ stream. In many olefins units this stream is hydrotreated to remove dienes and acetylenes and then sold as a gasoline blending component. However, because of its low octane content, the $C_5$ olefin/paraffin stream is of very low value. The stream can also be returned as feed to the olefin furnaces. The value as a feedstock in this application is also limited because the $C_5$ olefins tend to crack to yield undesirable products. This invention is a process whereby the $C_5$ olefins including cyclopentene are converted to more valuable products which do not boil in the $C_5$ range. Thus the $C_5$ paraffins can be isolated and used as feedstocks to the olefin furnaces.

It has long been known to contact various hydrocarbon fractions with acidic catalysts generally, and in particular, with siliceous acidic catalysts, including those referred to as crystalline aluminosilicate zeolites.

Zeolitic materials, both natural and synthetic, are many times known to have catalytic capabilities. Zeolitic materials typically are ordered porous crystalline aluminosilicates having a definite structure with cavities interconnected by channels. The cavities and channels throughout the crystalline material generally are uniform in size, allowing selective separation of hydrocarbons. Consequently, in many instances these materials are known in the art as "molecular sieves" and are used, in addition to selective adsorptive processes, for certain catalytic properties. The catalytic properties of these materials are affected to some extent by the size of the molecules which selectively penetrate the crystal structure, presumably to contact active catalytic sites within the ordered structure of these materials.

A wide variety of reactions have been carried out with zeolites including cracking, isomerization, hydrocracking, etc. Representative U.S. Patents disclosing and claiming contacting of various hydrocarbon fractions with crystalline aluminosilicates are U.S. Pat. Nos. 3,140,249; 3,140,251; 3,140,253; 3,140,322; 3,760,024; 3,894,102; 3,894,103; 3,894,104; 3,894,106; 3,907,663; 3,928,483; 4,012,455; and 4,150,062.

Boron is not considered a replacement for aluminum or silicon in a zeolitic composition. However, recently a new crystalline borosilicate molecular sieve AMS-1B with distinctive properties was disclosed in U.S. Pat. Nos. 4,268,420 and 4,269,813, incorporated by reference herein. According to these patents, AMS-1B can be synthesized by crystallizing a source of an oxide of silicon, an oxide of boron, an oxide of sodium, and an organic template compound such as a tetra-n-propyl ammonium salt. The process of this invention uses AMS-1B crystalline borosilicate molecular sieve.

The instant invention is concerned, not with hydrocarbons in general, but specifically with conversion of $C_5$ olefins, namely pentenes and cyclopentenes, in a hydrocarbon stream comprising predominantly pentanes and pentenes, to $C_6$-$C_{11}$ paraffins and olefins, aromatics and lighter olefins than pentenes. Additionally, the instant invention is concerned with recovery of the pentanes in the hydrocarbon stream as a desirable feed for steam cracking.

The formation of aromatic compounds from low molecular weight olefins is also known in the art but the selective formation of olefins from cyclopentenes and pentenes in the presence of pentanes wherein the pentanes are not converted to other hydrocarbons has not been previously known.

SUMMARY OF THE INVENTION

A process is disclosed whereby a low value $C_5$ hydrocarbon stream containing both olefins and paraffins is upgraded by catalytic conversion over an AMS-1B crystalline borosilicate catalyst or an AMS-1B crystalline borosilicate catalyst containing an ion or molecule of a catalytically active element, such as a noble metal. The $C_5$ olefins including cyclopentene are converted to aromatics and lighter olefins. After separation, the remaining $C_5$ hydrocarbons consist mainly of paraffins which are a desirable feedstock to steam crackers.

DETAILS OF THE INVENTION

This invention is a method to upgrade a low value $C_5$ stream containing n-pentane, isopentane, cyclopentane, cyclopentene and other pentenes to aromatic hydrocarbons, $C_3$-$C_4$ and $C_6$-$C_{11}$ paraffins and olefins by contacting the $C_5$ stream with a catalyst comprised of an AMS-1B crystalline borosilicate-based catalyst or an AMS-1B crystalline borosilicate catalyst containing an ion or molecule of a catalytically active element such as a noble metal. More particularly, this invention is a method to upgrade a $C_5$ stream containing n-pentane, isopentane, cyclopentane, cyclopentene and other pentenes to aromatics, $C_3$-$C_4$ and $C_6$-$C_{11}$ paraffins and olefins by contacting the $C_5$ stream with a catalyst comprised of the hydrogen form of an AMS-1B crystalline borosilicate catalyst or an AMS-1B crystalline borosilicate catalyst containing a platinum component.

In the process of this invention, a gaseous stream is passed through an AMS-1B crystalline borosilicate catalyst. Process parameters include temperatures of 150°14 650° C., pressure of 0.5 to 50 atmospheres of hydrocarbon and weight hourly space velocities (WHSV) of 0.2-20 grams feed/grams catalyst/hour. Preferred conditions for the borosilicate/alumina catalysts are 400°-550° C., 0.5-5 atmospheres and 0.5-5 grams feed/grams catalyst/hour. Higher temperature in these ranges results in higher conversions of $C_5$ olefins and lower formation of $C_6$+ olefins. Thus some flexibility is allowed the user of this process depending on the desired product slate. Non-$C_5$ paraffins and olefins are not harmful in the feedstock and other diluents such as inert gases, $H_2O$, CO, $CO_2$ can be used as well.

The catalyst useful in this invention is based on the crystalline borosilicate molecular sieve, AMS-1B, described in U.S. Pat. Nos. 4,268,420 and 4,269,813, incorporated herein by reference. A particularly useful catalyst for this invention contains the hydrogen form of AMS-1B in which a noble metal is placed by ion exchange, impregnation or other means.

The catalyst system which is useful in this invention comprises a borosilicate catalyst system based on a molecular sieve material identified as AMS-1B. Details as to the preparation of AMS-1B are described in U.S. Pat. No. 4,269,813 and European Published Application No. 68,796. Such AMS-1B crystalline borosilicate generally can be characterized by the X-ray pattern listed in Table 1 and by the composition formula $$0.9 \pm 0.2 M_{2/n}O:B_2O_3:ySiO_2:zH_2O$$

wherein M is at least one cation, n is the valence of the cation, y is between 4 and about 600, and z is between 0 and about 160.

TABLE 1

| d-Spacing Å[(1)] | Assigned Strength[(2)] |
|---|---|
| 11.2 ± 0 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

[(1)]Copper K alpha radiation
[(2)]VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

| | Broad | Preferred | Most Preferred |
|---|---|---|---|
| $SiO_2/B_2O_3$ | 5–400 | 10–150 | 10–80 |
| $R_2O-/[R_2O^- - M_{2/n}O]$ | 0.1–1.0 | 0.2–0.97 | 0.3–0.97 |
| $OH-/SiO_2$ | 0.01–11 | 0.1–2 | 0.1–1 |
| $H_2O/OH$ | 10–4000 | 10–500 | 10–500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blendor. After the pH is checked and adjusted, if necessary, the resulting slurry is transferred to a closed crystallization vessel for a suitable time. After crystallization, the resulting crystalline product can be filtered, washed with water, dried, and calcined.

Examples of oxides of silicon useful in this invention include silicic acid, sodium silicate, tetraalkyl silicates, and Ludox, a stabilized polymer of silicic acid manufactured by E. I. duPont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such cations usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. An example of an organic template is tetra-n-propyl ammonium bromide. Diamines, such as hexamethylenediamine, can be used.

The resulting crystalline product can be separated and recovered by well-known means such as filtration with washing. This material can be mildly dried from a few hours to a few days at varying temperatures, typically about 25°–200° C., to form a dry cake which can be crushed to a powder or to small particles and extruded, pelletized, or made into forms suitable for its intended use. Typically, the mildly dried product is calcined at temperatures ranging from about 260° C. to about 850° C., and preferably from about 525° C. to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Catalyst compositions useful in this invention preferably contain Group VIII elements while most preferably noble metals are used in this invention as catalytically active material. Such noble metals include ruthenium, osmium, rhodium, iridium, palladium and platinum; platinum and palladium are preferable while platinum is the most preferable. Mixtures of noble metals can be used.

In addition, preferable catalyst compositions are prepared containing a noble metal in combination with another metal ion or compound including Groups IB, IIB, IIIB, IVB, VB, VIB, VIIB and VIII metals and rare earth elements. Specific additional catalytic materials include ions and compounds of copper, lanthanum, molybdenum, cobalt, tungsten and nickel. Other additional catalytic materials can be ions and compounds of scandium, yttrium, titanium, zirconium, hafnium, vanadium, niobium, tantalum, chromium, cerium, manganese, iron, zinc and cadmium. Specific combinations of noble metal and other catalytic materials include ions or compounds of platinum and copper, platinum and lanthanum, platinum and cobalt, platinum and nickel, platinum and molybdenum, and platinum and tungsten.

Ion exchange and impregnation techniques are well-known in the art. Typically, an aqueous solution of a cationic species is exchanged one or more times at about 25° C. to about 100° C. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 weight percent to about thirty weight percent, typically from about 0.05 to about 25 weight percent, depending on the process use intended. The optimum amount can be determined easily by routine experimentation.

The AMS-1B crystalline borosilicate useful in this invention may be used as a pure material in a catalyst or may be admixed with or incorporated within various binders or matrix materials as disclosed in U.S. Pat. No. 4,433,190, incorporated herein by reference. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content may vary anywhere from a few up to 100 wt. % of the total composition. Catalytic compositions can contain about 0.1 wt. % to about 100 wt. % crystalline borosilicate material and preferably contain about 10 wt. % to about 95 wt. % of such material and most preferably contain about 20 wt. % to about 80 wt. % of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813.

In a process using this invention, a stream of $C_5$ hydrocarbons is contacted with a catalytic material-containing AMS-1B borosilicate-based catalyst. Generally, in the preferable process of this invention a $C_5$ hydrocarbon stream is contacted with the above-described AMS-1B borosilicate-based catalyst system in the liquid or vapor phase at a suitable reaction temperature, pressure and space velocity. Generally, suitable reaction conditions include a temperature of about 150° C. to about 650° C., a pressure of about 0.5 to about 50 atmospheres (50 to 5,000 kPa) or higher of hydrocarbon and weight hourly space velocities (WHSV) of 0.2–20 grams feed/grams catalyst/hour. Preferably, in a typical process scheme, a $C_5$-containing hydrocarbon stream is contacted with such catalyst in a reactor at about 400° C. to 550° C., at a pressure of from 0.5 to 5 atmospheres and 0.5 to 5 grams feed/grams catalyst/hour.

The hydrocarbon feed useful in this invention comprises a hydrocarbon stream substantially of $C_5$ hydrocarbons comprising n-pentane, isopentane, cyclopentane, cyclopentene and other pentenes. Non-$C_5$ paraffins and olefins can be present in the feeds as well as diluents such as water, carbon monoxide and carbon dioxide.

This invention is demonstrated but not limited by the following Examples.

EXAMPLES I–III

A hydrogen form of AMS-1B crystalline borosilicate catalyst was prepared according to the teachings of U.S. Pat. Nos. 4,269,813 and 4,433,190, to form a 40% hydrogen form of AMS-1B on alumina support.

The extrudate of 40% HAMS-1B on alumina support was crushed and sieved to yield particles with a diameter of 0.0164 to 0.0278 inches. A 5.0-gram sample of this catalyst was packed into the center of a stainless steel reactor (0.5 inch OD×18 inches long). A mixed-$C_5$ olefin/paraffin stream of composition similar to that produced in an olefins unit was used as feed to the reactor. As shown in Table II a single pass of the feed through the reactor converted 81–87% of the $C_5$ olefins. The cyclopentene was almost entirely converted. The selectivity to lighter olefins ranged from 38–62% and selectively to aromatics ranged from 20–29%. In Example III, the combined selectivity to light olefins and aromatics was 91% at a conversion level of 87%. In addition, the $C_5$ product contained ~90% paraffins compared to 63% in the feed and thus would be a desirable feedstock to the steam crackers. Details are in Table II.

TABLE II

C₅ Conversion Over 40% HAMS-1B/Al₂O₃

| Example | I | II | III |
|---|---|---|---|
| Sample 7631-22- | | 183/184 | 177/178 | 179/180 |
| Avg. Temp. (°C.) | | 394 | 443 | 491 |
| PSIG | | 1 | 1 | 1 |
| WHSV | | 2.5 | 2.0 | 2.0 |
| Composition Wt % | Feed | | | |
| Methane | — | 0.1 | 0.09 | 0.24 |
| Ethane | — | 0.04 | 0.19 | 0.43 |
| Ethylene | — | 0.59 | 1.40 | 2.56 |
| Propane | — | 0.43 | 1.37 | 2.23 |
| Propylene | — | 3.54 | 5.58 | 8.55 |
| Butanes | — | 1.26 | 2.46 | 2.24 |
| n-Butenes | — | 3.93 | 4.60 | 5.75 |
| Isobutylene | — | 3.68 | 3.78 | 3.94 |
| n-Pentane | 27.5 | 25.6 | 25.1 | 23.6 |
| Isopentane | 30.9 | 30.0 | 31.0 | 28.7 |
| Cyclopentane | 4.6 | 4.8 | 4.7 | 4.2 |
| Pentenes (except cyclo) | 25.2 | 6.1 | 4.7 | 4.5 |
| Cyclopentene | 13.2 | 1.27 | 0.34 | 0.32 |
| C₆-C₁₁ Paraffins + Olefins | — | 12.5 | 5.92 | 2.7 |
| Aromatics | — | 6.2 | 8.8 | 9.8 |
| % C₅ Olefin (C₅=) Converted | — | 81 | 87 | 87 |
| % C₂=-C₄= formed/C₅= Converted | — | 38 | 46 | 62 |
| % Aromatics formed/C₅= Converted | — | 20 | 26 | 29 |
| % Pentanes in C₅ Fraction | 63 | 89 | 92 | 92 |

EXAMPLES IV-VI

The following examples illustrate the conversion of a C₅ hydrocarbon stream using a catalyst of 40% HAMS-1B on alumina support containing 0.5 (wt) % platinum.

A catalyst was prepared by incorporating platinum in the form of Pt(NH₃)₄Cl₂ in the mixture of HAMS-1B and alumina sol prior to gellation. After gellation with NH₄OH, drying at 150° C. (4 hours), and calcination of 300° C. (4 hours), the catalyst was ground and sieved to obtain particles of 0.0164-0.0278 inch in diameter. A 5.0-gram sample of this material was packed into a reactor as in the previous examples and placed on-stream using the same C₅ mixture used in Examples I–III. With this active catalytic system the pentanes conversion became significant. Thus the combined production of light olefins and aromatics divided by the C₅ olefin conversion exceeds 100 percent.

In Examples V and VI authentic C₅ streams from commercially-operating olefins units were used. These examples illustrate that the catalyst system can withstand the impurities present in an authentic plant sample. Examples V and VI were taken after the catalyst had been regenerated once by an air burn at 500° C. Thus they also illustrate that the catalyst maintains activity after regeneration and several days (85 hours) on stream since the regeneration. Details are in Table III.

TABLE III

C₅ Conversion Over 40% HAMS-1B/Al₂O₃ With 0.5% Platinum

| Example | | IV |
|---|---|---|
| Sample 7631-88- | | 2/3 |
| Avg. Temp. (°C.) | | 495 |
| PSIG | | 1 |
| WHSV | | 2.5 |
| Hours On Stream Since Regeneration Cycle | | 12 First |
| Composition Wt % | Feed | |
| Methane | — | 0.68 |
| Ethane | — | 1.49 |
| Ethylene | — | 3.85 |
| Propane | — | 5.17 |
| Propylene | — | 9.71 |
| Butanes | — | 4.78 |
| n-Butenes | — | 5.15 |
| Isobutylene | — | 3.75 |
| n-Pentane | 25.7 | 17.5 |
| Isopentane | 30.9 | 25.3 |
| Cyclopentane | 4.64 | 1.99 |
| Pentenes (except cyclo) | 25.2 | 4.23 |
| Cyclopentene | 13.2 | 0.11 |
| C₆-C₁₁ Paraffins + Olefins | — | 1.97 |
| Aromatics | — | 14.4 |
| % C₅ Olefin (C₅=) Converted | | 89 |
| % C₂=-C₄= formed/C₅= Converted | | 66 |
| % Aromatics formed/C₅= Converted | | 42 |
| % Pentanes in C₅ fraction | 63 | 91 |

| Example | | V | VI |
|---|---|---|---|
| Sample 7631-88- | | 29/30 | 31/32 |
| Avg. Temp. (°C.) | | 448 | 496 |
| PSIG | | 1 | 1 |
| WHSV | | 1.9 | 1.9 |
| Hours On Stream Since Regeneration Cycle | | 85 Second | 89 Second |
| Composition Wt % | Feed | | |
| Methane | — | 0.08 | 0.29 |
| Ethane | — | 0.20 | 0.54 |
| Ethylene | — | 1.78 | 3.38 |
| Propane | — | 1.33 | 2.09 |
| Propylene | — | 7.00 | 10.2 |
| Butanes | — | 2.50 | 2.48 |
| n-Butenes | 0.77 | 5.51 | 5.97 |
| Isobutylene | | 4.47 | 4.65 |
| n-Pentane | 22.5 | 21.6 | 22.2 |
| Isopentane | 21.7 | 21.3 | 18.2 |
| Cyclopentane | 6.97 | 8.9 | 6.83 |
| Pentenes (except cyclo) | 27.6 | 5.17 | 4.92 |
| Cyclopentene | 16.8 | 0.48 | 0.71 |
| C₆-C₁₁ Paraffins + Olefins | 1.7 | 7.0 | 5.52 |
| Aromatics | — | 12.7 | 12.0 |
| % C₅ Olefin (C₅=) Converted | | 87 | 87 |
| % C₂=-C₄= formed/C₅= Converted | | 48 | 62 |
| % Aromatics formed/C₅= Converted | | 33 | 31 |
| % Pentanes in C₅ fraction | 51 | 90 | 89 |

What is claimed is:

1. A process to convert a C₅ hydrocarbon stream of C₅ paraffins and C₅ olefins to a stream containing a product fraction of at least about 50 (wt) % pentanes, said C₅ hydrocarbon stream comprising at least about 18 (wt) % C₅ paraffins and at least about 10 (wt) % cyclopentenes wherein at least about 70 (wt) % of said C₅ olefins are converted to C₃ to C₄ paraffins and olefins, C₆-C₁₁ paraffins and olefins and aromatic hydrocarbons wherein said process comprises contacting said C₅ hydrocarbon stream under conversion conditions comprising a temperature within the range of from about 150° C. to about 650° C., a pressure of from about 0.5 to 50 atmospheres and weight hourly space velocities (WHSV) of from 0.2 to about 20 grams feed per grams catalyst per hour with a catalyst comprising an AMS-1B crystalline borosilicate catalyst composition.

2. The process of claim 1 wherein said conversion conditions comprise a temperature within the range of from about 400° C. to about 550° C., a pressure within the range of from about 0.5 to about 5 atmospheres of said hydrocarbon stream and weight hourly space velocities of from about 0.5 to about 5 grams feed per grams catalyst per hour.

3. The process of claim 1 wherein said catalyst comprises an AMS-1B crystalline borosilicate catalyst composition containing an ion or a molecule of a noble metal.

4. The process of claim 3 wherein said noble metal is platinum or palladium.

5. The process of claim 4 wherein said noble metal is platinum.

6. The process of claim 1 wherein said catalyst comprises an AMS-1B crystalline borosilicate catalyst containing an ion or a molecule of a Group IB, IIIB, IVB, VB, VIB, VIIB or VIII metal or a rare earth element is contained in said MS-1B crystalline borosilicate catalyst as an additional catalytically active material.

7. The process of claim 6 wherein said additional catalytically active material is copper, lanthanum, molybdenum, cobalt, tungsten, nickel or zinc.

8. The process of claim 1 wherein said AMS-1B crystalline borosilicate content in said catalyst is present in a range of from about 10 to 95 (wt) %.

9. The process of claim 1 wherein said catalyst comprises an alumina content of from about 5 to 90 (wt) %

10. The process of claim 1 wherein said AMS-1B crystalline borosilicate catalyst is in the hydrogen form.

11. The process of claim 5 wherein said platinum is present in an amount of about 0.5 (wt) % of total catalyst weight.

* * * * *

UNITED STATES PATENT OFFICE
CERTIFICATE OF CORRECTION

Patent No. 4,777,311　　　　　　　　　　Dated　October 11, 1988

Inventor(s)　Sikkenga-Papadopoulos-Watson

It is certified that error appears in the above-identified patent and that said Letters Patent are hereby corrected as shown below:

| Column | Line | | |
|---|---|---|---|
| 2 | 47 | "150°14 650°C.," should read | --150°-650°C.,-- |
| 9 | 11 | "MS-1B" should read | -- AMS-1B -- |

Signed and Sealed this

Eighteenth Day of April, 1989

Attest:

DONALD J. QUIGG

Attesting Officer　　　　Commissioner of Patents and Trademarks